United States Patent [19]

Smith

[11] 4,048,239

[45] Sept. 13, 1977

[54] PROCESS FOR THE ORTHO ALKYLATION OF PHENOLS USING ALDEHYDES AND HYDROGEN IN THE PRESENCE OF A COPPER-CHROMIUM CATALYST

[75] Inventor: William Edward Smith, Schenectady, N.Y.

[73] Assignee: General Electric Company, Pittsfield, Mass.

[21] Appl. No.: 676,501

[22] Filed: Apr. 13, 1976

[51] Int. Cl.$^2$ .................... C07C 39/06; C07C 37/12
[52] U.S. Cl. ......................... 260/624 C; 260/624 R; 260/621 R; 260/619 R
[58] Field of Search ........... 260/624 C, 624 R, 621 R, 260/619, 619 R, 621 H

[56] References Cited

U.S. PATENT DOCUMENTS

| | | | |
|---|---|---|---|
| 2,194,215 | 3/1940 | Bruson et al. | 260/621 R |
| 2,401,608 | 6/1946 | Burawoy | 260/621 R |
| 3,592,951 | 7/1971 | Zaweski | 260/624 |

*Primary Examiner*—James O. Thomas, Jr.
*Assistant Examiner*—W. B. Lone
*Attorney, Agent, or Firm*—William F. Mufatti

[57] ABSTRACT

A process for selectively ortho-alkylating a phenolic compound which comprises reacting the phenolic compound with an aldehyde and hydrogen in the presence of a copper-chromium catalyst.

7 Claims, No Drawings

PROCESS FOR THE ORTHO ALKYLATION OF PHENOLS USING ALDEHYDES AND HYDROGEN IN THE PRESENCE OF A COPPER-CHROMIUM CATALYST

This invention is directed to a process for selectively orthoalkylating a phenolic compound which comprises reacting the phenolic compound with an aldehyde and hyrogen in the presence of a copper-chromium catalyst.

BACKGROUND OF THE INVENTION

It is well known in the art to alkylate phenols having at least one unsubstituted ortho position. Many prior art processes have been disclosed as being non-selective and indiscriminate in regard to the nature of the products that are formed. Winkler et al, U.S. Pat. No. 2,448,942, for example, discloses a process for the preparation of penta-substituted phenols. The Winkler et al patent mentions that one may employ either alcohol or methyl ether in the vapor phase using various metal oxides such as aluminum oxide, barium oxide, manganese oxide, magnesium oxide, calcium oxide, etc. as the catalyst. Alumina is the preferred catalyst. The Winkler et al process, however, is somewhat indiscriminate and lacks specificity for ortho-alkylation to the relative exclusion of alkylation in the meta- and para- positions.

Winkler et al teach that the reaction is carried out at super-atmospheric pressures at temperatures in the range of 300° to about 450° C. However, temperatures of about 430° C have been noted, e.g., in Hamilton, U.S. Pat. No. 3,446,856, to cause a decrease in the yield of alkylated product. When phenol and methanol are reacted at temperatures above 450° C, Hamilton teaches that the production of hexamethyl benzene, a non-phenolic product, is favored. For reactions of methanol with phenol, xylenol or cresol, Hamilton stated that a temperature of about 350° to 430° C is favored in order to obtain high yields of alkylated product, while temperatures below 350° C increase the yield of ether by-products. Temperatures of above 450° C and superatmospheric pressures cause decomposition of the reactant and favor the production of unwanted materials. The Hamilton process was based on the discovery that magnesium oxide was a selective ortho-alkylation catalyst that was useful at atmospheric pressure at a defined temperature range.

U.S. Pat. Nos. 3,707,569 and 3,751,488 are based respectively, on the discoveries that certain tellurium-containing compounds and molybdic acid salts are useful as selective ortho-alkylation catalysts. Further, U.S. Pat. No. 3,764,630 describes a method for selectively alkylating a phenol compound with an alkanol in the presence of water and a catalytically active compound such as molybdenum oxide and alkali metal, alkaline earth metal, lead, bismuth and ammonium salts of molybdic acid in admixture with magnesium oxide. Also, U.S. Pat. No. 3,843,606 discloses a catalyst which is porous magnesium oxide powder bonded with an inert organic cellulosic polymeric binder for use in selective alkylation of phenols. Lastly, U.S. Pat. No. 3,873,628 discloses mixtures of magnesium oxide and manganese sulfate as useful catalysts for orthoalkylation of phenols. These patents are incorporated herein by reference.

Ortho-alkylated phenols have valuable properties. They are particularly useful as the starting material for the manufacture of polyarylene ethers such as polyphenylene oxide, a valuable thermoplastic resin disclosed and claimed, for example, in A. S. Hay's U.S. Pat. No. 3,306,875.

DESCRIPTION OF THE INVENTION

In copending application of William E. Smith, Ser. No. 676,503 (attorney Docket No. 8CH-2415), filed on the same day as the present invention, titled "A PROCESS FOR THE SELECTIVE ORTHOALKYLATION OF A PHENOL IN THE PRESENCE OF A COPPER-CHROMIUM CATALYST" and assigned to the same assignee as the present invention, there is disclosed a process by which phenols and alkanols can be converted to the ortho-alkylated phenols with high selectivity and under mild conditions in the presence of a copper-chromium catalyst. The present invention is concerned with a process for selectively ortho-alkylating a phenolic compound which comprises reacting the phenolic compound with an aldehyde and hydrogen in the presence of a copper-chromium catalyst, as illustrated in Equation 1.

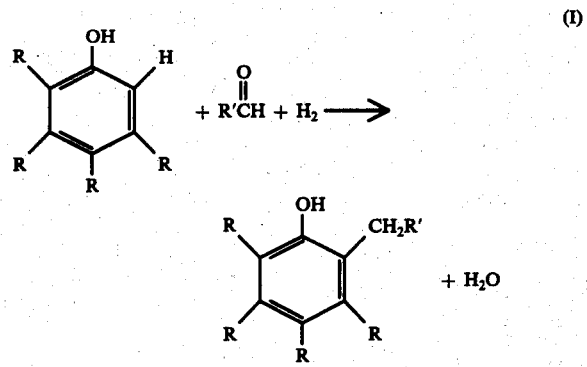

The phenolic compound is of the general formula:

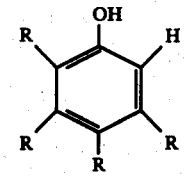

wherein each R is a monovalent substituent selected from the group consisting of hydrogen, alkyl of 1 to 12 carbon atoms, aryl of 6 to 12 carbon atoms and alkaryl of 7 to 12 carbon atoms. Examples of these substituents include methyl, ethyl, n-propyl, phenyl, o-methylphenyl, p-methylphenyl, 2,6-xylyl, and the like. Especially useful starting materials are phenol, o-cresol, m-cresol, p-cresol, o-phenylphenol and 3,5-xylenol. The preferred embodiment of the process is carried out using phenol, ortho cresol, or a mixture of the two as the phenolic starting material.

Suitable aldehydes may be represented by the formula:

wherein R' is hydrogen or is an alkyl or alkenyl radical of up to about 12 carbon atoms, straight chain or branched chain. Illustrative aldehydes are those wherein R' is methyl, ethyl, n-propyl, i-propyl, n-butyl, t-butyl, hexyl, octyl, 2-ethylhexyl, decyl, dodecyl, or vinyl. Preferred aldehydes are acetaldehyde, formaldehyde, propionaldehyde and acrolein.

In order to obtain the maximum yield of ortho-alkylated products, it is preferred to use at least 0.5 mole of aldehyde, and preferably from 1 to 3 moles of aldehyde for each ortho position hydrogen in the phenolic compound to be alkylated. For example, if phenol is to be methylated to produce a maximum yield of 2,6-xylenol (2,6-dimethylphenol), it is preferred to use at least 2 moles and especially preferred to use from 2 to 6 moles of formaldehyde for each mole of phenol along with a corresponding amount of hydrogen. Of course, if the phenolic compound is already monosubstituted in one of the ortho positions, maximum yields will be obtained with at least one mole of aldehyde, e.g., formaldehyde, per mole of phenolic compound, e.g., ortho cresol. The hydrogen serves the multiple purposes of stoichoimetric reactant, catalyst activator and carrier gas.

The catalysts of the present invention are copper-chromium oxide compositions, either as amorphous mixed oxides, or as crystalline copper chromite substances such as those described in H. Charcosset et al, *Compt. Rend;* 254,2990-2 (1962), or as mixtures of the amorphous and crystalline substances. The copper-chromium catalysts of the instant invention can be varied in composition from about 0.05 parts to about 10 parts of copper per part of chromium. In a preferred embodiment, the copper-chromium oxide compositions are promoted by the presence of a component selected from the oxides and hydroxides of the Group I, II or III metals, manganese, iron and mixtures thereof. These promoters can constitute from about 3 to about 95% of the catalyst composition.

The catalysts of the instant invention may be prepared by a number of different methods, such as those described in U.S. Pat. No. 3,899,446, for example, which is incorporated herein by reference. An Example in this patent describes the preparation of a copper-chromium-zinc mixed oxide composition, which after reduction is effective in bringing about the selective ortho methylation of phenol and ortho cresol by formaldehyde and hydrogen. Alternatively, standard copper chromite or copper chromite precursor compositions can be promoted by impregnation with suitable metal oxides, hydroxides, carbonates, formates and the like and heating in place. In another method, copper and chromium oxides can be coprecipitated with such other promoters as zinc oxide, barium oxide, manganese oxide, cadmium oxide, magnesium oxide and the like.

In another variation, the catalyst of the instant invention can be composed of mixed pellet types. For example, a bed of copper chromite pellets mixed with magnesium oxide or zinc oxide pellets can be employed.

The catalyst is preferably used in the form of a bed through which the reactants are passed in the vapor phase. Preferred pressures are in the range from about atmospheric to about 5 atmospheres.

The instant process is carried out at a temperature of at least 185° C. The optimum alkylation temperature is in the range of from 185° to about 400° C.

The instant process may be carried out by using a variety of reactors with varying flow rates of the reactants, varying vapor space velocities of the reactants and length of the catalyst bed. Tubular reactors, such as a glass or a metal tube filled with a bed of the catalyst may be employed. The reactor is heated with conventional means either by surrounding the reactor with an electrical heater, a heated gas, or a fused salt bath, liquid metal etc., which can be conveniently maintained at reaction temperature by the use of immersion type electrical heaters. Alternatively, a fluid bed reactor may be used. The alkylation reaction is exothermic and, therefore, the heat of reaction can be utilized to maintain the catalyst bed at the proper reaction temperature.

The techniques are conventional and reference is made to the above-mentioned patents.

In carrying out an alkylation in accordance with the invention, any one or a mixture of phenols having an ortho hydrogen together with an aldehyde may be vaporized and passed with hydrogen through a reactor heated to a temperature of at least 185° C containing the copper-chromium catalyst of the invention. The aldehyde can be mixed with the phenol to form a solution which is then vaporized or separate streams of the two reactants may be fed to the same or separate vaporizers and then to said reactor.

The vapors issuing from the reactor are condensed in the usual fashion and the products separated in the usual fashion, for example, by crystallization, distillation, etc.

DESCRIPTION OF THE PREFERRED EMBODIMENT

The following examples are set forth to illustrate more clearly the principle and practice of this invention to those skilled in the art. Unless otherwise specified where parts or percents are mentioned, they are parts or percents by weight.

Apparatus. Two vertical hot tube reactors (16 mm ID × 70 cm effective length, 130 cc effective volume; and 20 mm ID × 30 cm effective length, 70 cc effective volume) were constructed from heavy wall glass, with 24/40 male and female joints. Vigreaux points were indented just above the male joint to support catalyst pellets. Thermocouple leads were fastened into three other Vigreaux indentations at points along the length. Briskheat glass insulating heating tapes were wound onto the tube, covered with glass wool and glass tape, and connected to separate variable transformers. The tube exit was connected by a gooseneck (also heated) to an efficient condenser and collection vessel. An electrically heated three-necked flask served as the evaporator, with the reactants added through a side neck by a syringe pump. A hydrogen stream (one bed volume per minute) served as a carrier gas.

EXAMPLE I

Ortho Ethylation of Phenol Via Acetaldehyde. The 130 ml reactor was charged with a catalyst prepared by impregnating 192 grams of copper chromite (Catalysts and Chemicals, Inc., 3/16 inch pellets containing 34% Cu, 30.7% Cr and 5.7% Ba as the oxides) with 19.2 grams of zinc formate using an aqueous rotary evaporative technique. Heating the bed to 300° C under hydrogen resulted in activation of the copper chromite component and pyrolysis of the zinc formate to zinc oxide (about 5% by weight of the active catalyst).

A mixture of acetaldehyde and phenol (3:1 molar proportions, prepared using 88% phenol — 12% water) was passed into the evaporator at 36 ml/hr (LHSV = 0.28) under hydrogen, with the catalyst bed maintained at 250°. After equilibrium was established a steady ethylation with high selectivity (95%) to ortho substituted products was effected. A glpc analysis of the effluent produced at the eighth hour of operation showed a phenol conversion of 19%; the phenolic products were 2-ethylphenol (90%), 2,6-diethylphenol (5%), 4-ethylphenol (4%) and 2,4-diethylphenol (1%). Both acetaldehyde and ethanol, in approximately equal proportions, were present in the effluent. All structure assignments were confirmed by glpc-mass spectral analysis.

EXAMPLE II

Ortho Methylation of Phenol Via Formaldehyde. The reactor, catalyst bed and general procedure described above were employed, using a formalin-phenol feed (2:1 formaldehyde/phenol, some methanol and water present) passed in at the 0.28 LHSV and 250° operating temperature. The effluent contained phenol, o-cresol and 2,6-xylenol in about 85:14:1 molar ratio. A significant amount of what was apparently a phenol-formaldehyde resin accumulated in the evaporator.

EXAMPLE III

Ortho n-Propylation Via Acrolein. The reactor, catalyst bed and general procedure described above were employed, using a 3:1 acrolein-phenol feed passed in at the LHSV of 0.28. Steady state operation at 250° resulted in conversion of about 10% of the phenol per pass, with 2-n-propylphenol as the sole phenolic product. At 300° the phenol conversion was 21% per pass; the products were 2-n-propylphenol (93%) and 2,6-di-n-propylphenol (7%). Propionaldehyde and propanol as well as unconverted acrolein were detected in the effluent.

EXAMPLE IV

Ortho n-Propylation Via Propionaldehyde. The reactor and general procedure described above were employed with 130 cc of a catalyst prepared from Girdler G-13 copper chromite (3/16 × 3/16 inch pellets containing 40% Cu and 25.5% Cr as oxides) and 10% by weight of zinc formate. After activation a 3:1 propionaldehydephenol mixture was passed through with hydrogen at 300° C. Analysis of the effluent showed that about 9% of the phenol had been converted to 2-n-propylphenol.

Obviously, other modifications and variations of the present invention are possible in the light of the above teachings. It is, therefore, to be understood that cahnges may be made in the particular embodiments of the invention described which are within the full intended scope of the invention as defined by the appended claims.

What is claimed is:
1. A process for the selective ortho-alkylation of a phenolic compound of the general formula:

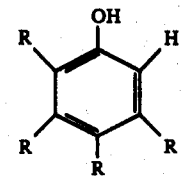

wherein each R is a monovalent substitutent selected from the group consisting of hydrogen, alkyl of 1 to 12 carbon atoms, aryl of 6 to 12 carbon atoms and alkaryl of 7 to 12 carbon atoms, the process comprising reacting at a temperature of from about 185° to about 400° C in the presence of a copper-chromium oxide catalyst said phenolic compound with hydrogen and an aldehyde represented by the formula

wherein R' is hydrogen or an alkyl or alkenyl radical of up to about 12 carbon atoms, straight or branched chain, with said copper-chromium oxide catalyst being chosen from the group consisting of crystalline copper chromites, amorphous mixed oxides of copper and chromium, and mixtures thereof.

2. A process as defined in claim 1 wherein each R is hydrogen.

3. A process as defined in claim 1 wherein the aldehyde is selected from the group consisting of acetaldehyde, formaldehyde, propionaldehyde and acrolein.

4. The process of claim 1 wherein the copper-chromium catalyst is copper chromite.

5. The process as defined in claim wherein the copper-chromium oxide catalyst is admixed with a promoter selected from the oxides and hydroxides of Group I, II or III metals, manganese, iron, or mixtures thereof.

6. The process as defined in claim 5 wherein the catalyst is in the form of copper chromite pellets admixed with pellets of the oxides of Group I, II or III metals, manganese, iron, and mixtures thereof.

7. The process as defined in claim 5 wherein the promoter is zinc oxide.

* * * * *

UNITED STATES PATENT AND TRADEMARK OFFICE
CERTIFICATE OF CORRECTION

PATENT NO. : 4,048,239
DATED : September 13, 1977
INVENTOR(S) : William Edward Smith It is certified that error appears in the above-identified patent and that said Letters Patent are hereby corrected as shown below:

Claim 4, line 2, after "chromium" insert -- oxide --

Claim 5, line 1, after "claim" insert -- 1 --

Signed and Sealed this

Third Day of January 1978

[SEAL]

Attest:

RUTH C. MASON
*Attesting Officer*

LUTRELLE F. PARKER
*Acting Commissioner of Patents and Trademarks*